United States Patent
Su et al.

(10) Patent No.: US 7,947,649 B2
(45) Date of Patent: May 24, 2011

(54) LIQUID BUFFERED GDF-5 FORMULATIONS

(75) Inventors: Dongling Su, Franklin, MA (US); Julius Lopez, Dorchester, MA (US)

(73) Assignee: Advanced Technologies and Regenerative Medicine, LLC, Raynham, MA (US)

( * ) Notice: Subject to any disclaimer, the term of this patent is extended or adjusted under 35 U.S.C. 154(b) by 18 days.

(21) Appl. No.: 12/420,260

(22) Filed: Apr. 8, 2009

(65) Prior Publication Data

US 2009/0259023 A1    Oct. 15, 2009

Related U.S. Application Data

(60) Provisional application No. 61/044,518, filed on Apr. 14, 2008.

(51) Int. Cl.
| | |
|---|---|
| A61K 38/00 | (2006.01) |
| A61K 38/16 | (2006.01) |
| A61K 38/17 | (2006.01) |
| A61K 38/18 | (2006.01) |
| C07K 14/00 | (2006.01) |
| C07K 14/435 | (2006.01) |
| C07K 14/46 | (2006.01) |
| C07K 14/47 | (2006.01) |
| C07K 14/475 | (2006.01) |

(52) U.S. Cl. ......... 514/8.9; 514/7.6; 530/350; 530/399; 530/412

(58) Field of Classification Search ............ None
See application file for complete search history.

(56) References Cited

U.S. PATENT DOCUMENTS

| | | |
|---|---|---|
| 2,931,802 A | 4/1960 | Touey |
| 4,120,810 A | 10/1978 | Palmer |
| 4,891,319 A | 1/1990 | Roser |
| 5,011,691 A | 4/1991 | Oppermann et al. |
| 5,013,649 A | 5/1991 | Wang |
| 5,202,311 A | 4/1993 | Folkman et al. |
| 5,231,169 A | 7/1993 | Constantz |
| 5,266,683 A | 11/1993 | Oppermann et al. |
| 5,318,898 A | 6/1994 | Israel |
| 5,385,887 A | 1/1995 | Yim |
| 5,411,941 A | 5/1995 | Grinna |
| 5,455,231 A | 10/1995 | Constantz |
| 5,516,654 A | 5/1996 | Israel |
| 5,658,882 A | 8/1997 | Celeste |
| 5,747,058 A | 5/1998 | Tipton |
| 5,770,700 A | 6/1998 | Webb et al. |
| 5,776,193 A | 7/1998 | Kwan |
| 5,801,014 A | 9/1998 | Lee |

(Continued)

FOREIGN PATENT DOCUMENTS

EP    0955313 A1    11/1999

(Continued)

OTHER PUBLICATIONS

Triantfilou, et al., Nature Immunology 2, 338-345 (2001).

(Continued)

*Primary Examiner* — Elizabeth C Kemmerer

(57) ABSTRACT

Improved formulations and methods are provided for stabilizing a solution of bone morphogenetic protein. The compositions comprise an acetate buffered solution of GDF-5 and other excipients wherein the solution has a pH of from about 4.2 to about 5.3, thereby providing for a biologically isotonic solution having improved stability of the GDF-5 protein during storage, handling, and use.

14 Claims, 12 Drawing Sheets

Stability of 0.1 mg/ml rhGDF-5 in 5 mM acetate buffer solution at pH 4.5 after 32 days storage at 37 degrees Celsius, as evidenced by HPLC.

U.S. PATENT DOCUMENTS

| | | | |
|---|---|---|---|
| 5,804,557 A | 9/1998 | Cleland | |
| 5,866,165 A | 2/1999 | Liu | |
| 5,955,448 A | 9/1999 | Colaco | |
| 5,968,542 A | 10/1999 | Tipton | |
| 5,972,385 A | 10/1999 | Liu | |
| 5,985,320 A | 11/1999 | Edwards | |
| 6,051,558 A | 4/2000 | Burns | |
| 6,071,428 A | 6/2000 | Franks | |
| 6,165,981 A | 12/2000 | Flaa | |
| 6,171,584 B1 | 1/2001 | Hotten et al. | |
| 6,171,586 B1 | 1/2001 | Lam | |
| 6,187,742 B1 | 2/2001 | Wozney | |
| 6,207,718 B1 | 3/2001 | Papadimitriou | |
| 6,281,195 B1 | 8/2001 | Rueger | |
| 6,284,872 B1 | 9/2001 | Celeste | |
| 6,288,043 B1 * | 9/2001 | Spiro et al. | 514/54 |
| 6,340,369 B1 | 1/2002 | Ferree | |
| 6,344,058 B1 | 2/2002 | Ferree | |
| 6,352,557 B1 | 3/2002 | Ferree | |
| 6,407,060 B1 * | 6/2002 | Charette et al. | 514/12 |
| 6,419,702 B1 | 7/2002 | Ferree | |
| 6,454,804 B1 | 9/2002 | Ferree | |
| 6,551,801 B1 | 4/2003 | Andou et al. | |
| 6,645,247 B2 | 11/2003 | Ferree | |
| 6,648,918 B2 | 11/2003 | Ferree | |
| 6,648,919 B2 | 11/2003 | Ferree | |
| 6,648,920 B2 | 11/2003 | Ferree | |
| 6,656,492 B2 | 12/2003 | Kajiyama | |
| RE38,385 E | 1/2004 | Franks et al. | |
| 6,685,695 B2 | 2/2004 | Ferree | |
| 6,719,968 B2 | 4/2004 | Celeste | |
| 6,723,170 B2 | 4/2004 | Ohashi | |
| 6,755,863 B2 | 6/2004 | Ferree | |
| 6,764,994 B1 | 7/2004 | Hotten et al. | |
| 6,780,324 B2 | 8/2004 | Le Garrec | |
| 6,911,411 B2 | 6/2005 | Cox | |
| 6,936,582 B1 | 8/2005 | Charette | |
| 6,991,790 B1 | 1/2006 | Lam | |
| 6,992,065 B2 | 1/2006 | Okumu | |
| 7,060,268 B2 | 6/2006 | Andya et al. | |
| RE39,497 E | 2/2007 | Franks et al. | |
| 7,235,527 B2 | 6/2007 | Makishima et al. | |
| 7,318,840 B2 | 1/2008 | McKay | |
| 7,323,445 B2 | 1/2008 | Zhang | |
| 7,375,077 B2 | 5/2008 | Mao | |
| 7,435,260 B2 | 10/2008 | Ferree | |
| 7,572,440 B2 | 8/2009 | Vukicevic | |
| 7,678,764 B2 | 3/2010 | Garigapati | |
| 2001/0024823 A1 | 9/2001 | Vukicevic | |
| 2002/0032155 A1 | 3/2002 | Ferree | |
| 2002/0128718 A1 | 9/2002 | Ferree | |
| 2002/0165542 A1 | 11/2002 | Ferree | |
| 2002/0173770 A1 | 11/2002 | Flory | |
| 2003/0026788 A1 | 2/2003 | Ferree | |
| 2003/0185812 A1 | 10/2003 | Ferree | |
| 2003/0192554 A1 | 10/2003 | Ferree | |
| 2004/0022771 A1 | 2/2004 | Ferree | |
| 2004/0024471 A1 | 2/2004 | Ferree | |
| 2004/0028733 A1 | 2/2004 | Tracy et al. | |
| 2004/0132653 A1 | 7/2004 | Ichikawa | |
| 2004/0146923 A1 | 7/2004 | Celeste | |
| 2004/0197324 A1 | 10/2004 | Liu | |
| 2005/0069571 A1 | 3/2005 | Slivka | |
| 2005/0119754 A1 | 6/2005 | Trieu | |
| 2005/0191248 A1 | 9/2005 | Hunter | |
| 2006/0024346 A1 | 2/2006 | Brody et al. | |
| 2006/0088565 A1 * | 4/2006 | Kohnert et al. | 424/422 |
| 2006/0121113 A1 | 6/2006 | Bartholomaeus | |
| 2006/0223120 A1 | 10/2006 | Kim et al. | |
| 2006/0286171 A1 | 12/2006 | Zhou | |
| 2006/0286289 A1 | 12/2006 | Prajapati | |
| 2006/0287676 A1 | 12/2006 | Prajapati | |
| 2007/0053871 A1 | 3/2007 | Li | |
| 2007/0098756 A1 | 5/2007 | Behnam | |
| 2007/0172479 A1 | 7/2007 | Warne | |
| 2007/0178159 A1 | 8/2007 | Chen | |
| 2008/0098614 A1 | 5/2008 | Tchessalov | |
| 2008/0147077 A1 | 6/2008 | Garigapati | |
| 2008/0234727 A1 | 9/2008 | Garigapati | |
| 2008/0311078 A1 | 12/2008 | Gokarn | |
| 2009/0004048 A1 | 1/2009 | Elliott | |
| 2009/0030483 A1 | 1/2009 | Risi | |
| 2009/0043078 A1 | 2/2009 | Daniel | |
| 2009/0048412 A1 | 2/2009 | Soula | |
| 2009/0060976 A1 | 3/2009 | Rueger | |
| 2009/0099089 A1 | 4/2009 | Zhang | |
| 2009/0286764 A1 | 11/2009 | Kipp | |
| 2009/0291062 A1 | 11/2009 | Fraunhofer | |
| 2010/0015230 A1 | 1/2010 | Ron | |
| 2010/0041870 A1 | 2/2010 | Tchessalov | |
| 2010/0130730 A1 | 5/2010 | Garigapati | |
| 2010/0144631 A1 | 6/2010 | Ron | |
| 2010/0255100 A1 | 10/2010 | Margolin | |

FOREIGN PATENT DOCUMENTS

| | | |
|---|---|---|
| EP | 957943 A1 | 5/2003 |
| EP | 1350525 A2 | 10/2003 |
| EP | 1462126 A | 9/2004 |
| EP | 1448246 B1 | 8/2005 |
| EP | 1274459 B1 | 11/2005 |
| EP | 1604693 A1 | 12/2005 |
| EP | 1604963 A2 | 12/2005 |
| EP | 955313 B1 | 5/2006 |
| EP | 1915986 A | 4/2008 |
| EP | 1932519 A1 | 6/2008 |
| EP | 957943 B2 | 11/2008 |
| WO | WO8800205 A1 | 1/1988 |
| WO | WO9011366 A1 | 10/1990 |
| WO | WO9118098 A1 | 11/1991 |
| WO | WO9200382 A1 | 1/1992 |
| WO | WO9309229 A1 | 5/1993 |
| WO | WO9316099 A2 | 8/1993 |
| WO | WO9410203 A2 | 5/1994 |
| WO | WO9415949 A1 | 7/1994 |
| WO | WO9415965 A1 | 7/1994 |
| WO | WO9415966 A1 | 7/1994 |
| WO | WO9421681 A1 | 9/1994 |
| WO | WO9426892 A1 | 11/1994 |
| WO | WO9426893 A1 | 11/1994 |
| WO | WO9501801 A1 | 1/1995 |
| WO | WO95/04819 | 2/1995 |
| WO | WO9504819 A1 | 2/1995 |
| WO | WO9510539 A1 | 4/1995 |
| WO | WO9510802 A1 | 4/1995 |
| WO | WO9516035 A2 | 6/1995 |
| WO | WO9533830 A1 | 12/1995 |
| WO | WO9601316 A1 | 1/1996 |
| WO | WO9601845 A1 | 1/1996 |
| WO | WO96/14335 A1 | 5/1996 |
| WO | WO9636710 A1 | 11/1996 |
| WO | WO0178683 A2 | 10/2001 |
| WO | WO03000282 A1 | 1/2003 |
| WO | WO03030923 A1 | 4/2003 |
| WO | WO03/043673 A | 5/2003 |
| WO | WO03066120 A1 | 8/2003 |
| WO | WO2004037265 A1 | 5/2004 |
| WO | WO2004052336 A2 | 6/2004 |
| WO | WO2005060989 A1 | 7/2005 |
| WO | WO2005100399 A2 | 10/2005 |
| WO | WO2005107765 A2 | 11/2005 |
| WO | WO2005115438 A1 | 12/2005 |
| WO | WO2006138099 A2 | 12/2006 |
| WO | WO2006138181 A2 | 12/2006 |
| WO | WO2007025441 A1 | 3/2007 |
| WO | WO2006138099 A3 | 10/2007 |
| WO | WO2008009419 A1 | 1/2008 |
| WO | WO2008045498 A1 | 4/2008 |
| WO | WO2008049588 A1 | 5/2008 |
| WO | WO2008079672 A2 | 7/2008 |
| WO | WO2008082563 A2 | 7/2008 |
| WO | WO2008099190 A2 | 8/2008 |
| WO | WO2008099198 A2 | 8/2008 |
| WO | WO2008082563 A3 | 11/2008 |
| WO | WO2008143867 A1 | 11/2008 |
| WO | WO2008079672 A3 | 12/2008 |
| WO | WO2009/006097 | 1/2009 |
| WO | WO2008099198 A3 | 1/2009 |

| WO | WO2009006097 A1 | 1/2009 |
| WO | WO2009006301 A2 | 1/2009 |
| WO | WO2009015736 A1 | 2/2009 |
| WO | WO2009016131 A1 | 2/2009 |
| WO | WO2009016333 A1 | 2/2009 |
| WO | WO2009020744 A1 | 2/2009 |

OTHER PUBLICATIONS

Massague, et al., Annual Review of Cell Biology 6:957 (1990).
Sampath, et al., Journal of Biological Chemistry 265:13198 (1990).
Celeste et al. PNAS 87:9843-47 (1990).
Ruppert et al., Eur J. Biochem 237, 295-302, (1996).
Honda et al., Journal of Bioscience and Bioengineering 89(6), 582-589 (2000).
European Search Report for Application No. PCT/US2009/039925 dated Aug. 10, 2009.
Letter from Keith E. Gilman of Lerner David Littenberg Krumholz & Mentlik LLP, dated Sep. 13, 2010 regarding Johnson & Johnson U.S. Publication No. 2008/0147077A1.
PCT Search Report dated Jul. 10, 2008 for application No. PCT/US2008/068007.
EP Search Report 07254571.8, May 8, 2008.
Basler et al., Control of Cell Pattern in the Neural Tube: Regulation of Cell Differentiation by dorsalin-1, a Novel TGFβ Family Member, Cell, 1993, 687-702, 73.
Dayhoffel et al., A Model of Evolutionary Change in Proteins, Atlas of Protein Sequence and Structure, 1978, pp. 354-352, vol. Suppl 3.
Lee et al., Expression of growth/differentiation factor 1 in the nervous system: Conservation of a bicistronic structure, Proc. Natl. Acad. Sci 88:4250-4254, 1991.
Mangram, Guideline for Prevention of Surgical Site Infection, Infection Control and Hospital Epidemiology, 1999, vol. 20, No. 4, 250-278).
Mazzocca, Tendon and Bone Cell Reponses to a Novel Suture Material, American Academy of Orthopedic Surgeons, Abstract #338 2005.
Needleman et al., A General Method Applicable to the Search for Similarities in the Amino Acid Sequence of Two Proteins, J. Mol. Biol. 1970, 443-453, vol. 48.
Padgett et al., A transcript from a *Drosophila* pattern gene predicts a protein homologous to the transforming growth factor-B family, Nature 1987, 81-84, vol. 325.
Peterson, et al., The Effect of Locally Vascular Endothelial Growth Factor on Meniscus Healing, 51st Annual Meeting of the Orthopedic Research Society, No. 0076.
Rickert et al., A Growth and Differentiation Factor-5 (GDF-5)-coated Suture Stimulates Tendon healing in an Achilles Tendon Model in Rats, Growth Factors, vol. 19, 2001, 115-126.
Rothenberger, In Vitro Antimicrobial Evaluation of Coated VICRYL* Plus Antibacterial Suture (Coated Polyglactin 910 with Triclosan) using Zone of Inhibition Assays, Surgical Infection Society Journal Supp, Dec. 2002, p. S79-87.
Schmidmaier, G, et al., Biodegradable Poly(D,L-Lactide) Coating of Implants for Continuous Release of Growth Factors, Biomedical Materials Res Appl Biomat, 58, 449-455, 2001.
Storm et al., Limb alterations in brachypodism mice due to mutations in a new member of the TGFβ-superfamily, Nature 368:639-643 1994.
Takao et al., Identification of Rate Bone Morphogenetic Protein-3b (BMP-3b), a New Member of BMP-3, Biochemical and Biophysical Research Communications, 219:656-662, 1996.
Von Heijne, A new method for predicting signal sequence cleavage sites, Nucleic Acids Research, 14:4683-4691 (1986).
Weeks, A Maternal mRNA Localized to the Vegetal Hemisphere in Zenopus Eggs Codes for a Growth Factor Related to TGF-β, Cell, vol. 51, 861-867, 1987.
Wozney et al., Novel Regulators of Bone Formation: Molecular Clones and Activities, Science 1988, 1528-1534, vol. 242.
Wright, Meniscal Healing Using Butyric Acid Impregnated Sutures, 50th Annual Meeting of the Orthopedic Research Society, #1234 2004.
Arakawa et al., 2001, Adv. Drug Delivery Rev. 46:307-326.
Arakawa et al., Pharmaceutical Research "Protein-Solvent Interactions in Pharmaceutical Formulations", vol. 8, No. 3, 1991, pp. 285-291.
Brus, C. et. al., "Stabilization of Oligonucleotide—Polyethylenimine Complexes by Freeze-Drying: Physicochemical and Biological Characterization". Journal of Controlled Release, Feb. 20, 2004, vol. 95, Issue 1, pp. 119-131.
Cheng, Hongwei. "Osteogenic Activity of the Fourteen Types of Human Bone Morphogenic Proteins", Journal Bone Joint Surgery Am. 85A, 2003, pp. 1544-1552.
Costantino, Henry R. et. al., "Effect of Excipients on the Stability and Structure of Lyophilized Recombinant Human Growth Hormone", Journal of Pharmaceutical Sciences, 1998, vol. 87, Issue 11, pp. 1412-1420.
Crowe, J., "Stabilization of Dry Phospholipid Bilayers and Proteins by Sugars", Biochem. J., 1987, 242, pp. 1-10.
Crowe, J., "The Trehalose Myth Revisited: Introduction to a Symposium on Stabilization of Cells in the Dry State", Crybiology, vol. 43, Issue 2, Sep. 2001, pp. 89-105.
Gloger, O., "Lyoprotection of Aviscumine with Low Molecular Weight Dextrans", International Journal of Pharmaceutics, Jul. 9, 2003, vol. 260, Issue 1, pp. 59-68.
Goodnough, M C, et. al., "Stabilization of Botulinum Toxin Type A During Lyophilization", Applied Environmental Microbiology, 1992, vol. 58, Issue 10, pp. 3426-3428.
Higashiyama et al., 2002, Pure Appl. Chem. 74:1263-1269.
Lories, Rik, J. U., "Bone Morphogenetic Protein Signaling in Joint Homeostasis and Disease", Cytokine Growth Factor Review, vol. 16, Issue 3, 2005, pp. 287-298.
Lyons, K et. al., "Vgr-1, a Mammalian Gene Related to *Xenopus* Vg-1, is a M Member of the Transforming Growth Factor Beta Gene Superfamily", Proceedings of the National Academy of Science, 1989, vol. 86, Issue 12, pp. 4554-4558.
Massague, J., "The Transforming Growth Factor-beta Family", Annual Review of Cell Biology, Nov. 1990, vol. 6, pp. 597-641.
Nakamoto et al., Feb. 2007, Cell Mol Life Sci 64(3):294-306.
Ozkaynak et. al., "OP-1 cDNA Encodes an Osteogenic Protein in the TGF-Beta Family". EMBO Journal, 1990, vol. 9, Issue 7, pp. 2085-2093.
Wang et al., 1999, Int. J. Pharmaceutics 185:129-188.
Wharton, Ka et. al., "*Drosophila* 60A Gene, Another Transforming Growth Factor Beta Family Member, is Closely Related to Human Bone Morphogenetic Proteins", Proceedings of the National Academy of Science, 1991, vol. 88, Issue 20, pp. 9214-9218.
Yancey, Paul, "Organic Osmolytes as Compatible, Metabolic and Counteracting Cytoprotectants in High Osmolarity and Other Stresses" Journal of Experimental Biology, 2005, vol. 208, pp. 2819-2830.
Ramos et. al., "Stabilization of Enzymes Against Thermal Stress and Freeze-Drying by Mannosylglycerate", Appl. Envir. Microiol. 1997, vol. 63, Issue 10, pp. 4020-4025.
Gupta et al., Lectin anchored stabilized biodegradable nanoparticles for oral immunization, Intl J Pharm 318 (2006) 163-173.

* cited by examiner

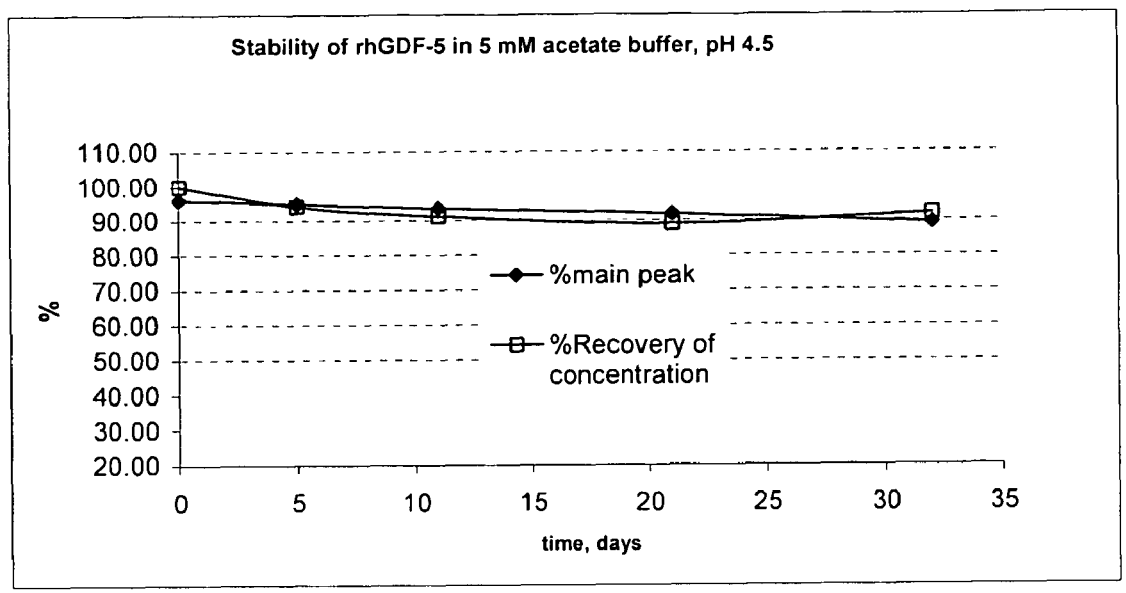
Figure 1. Stability of 0.1 mg/ml rhGDF-5 in 5 mM acetate buffer solution at pH 4.5 after 32 days storage at 37 degrees Celsius, as evidenced by HPLC.

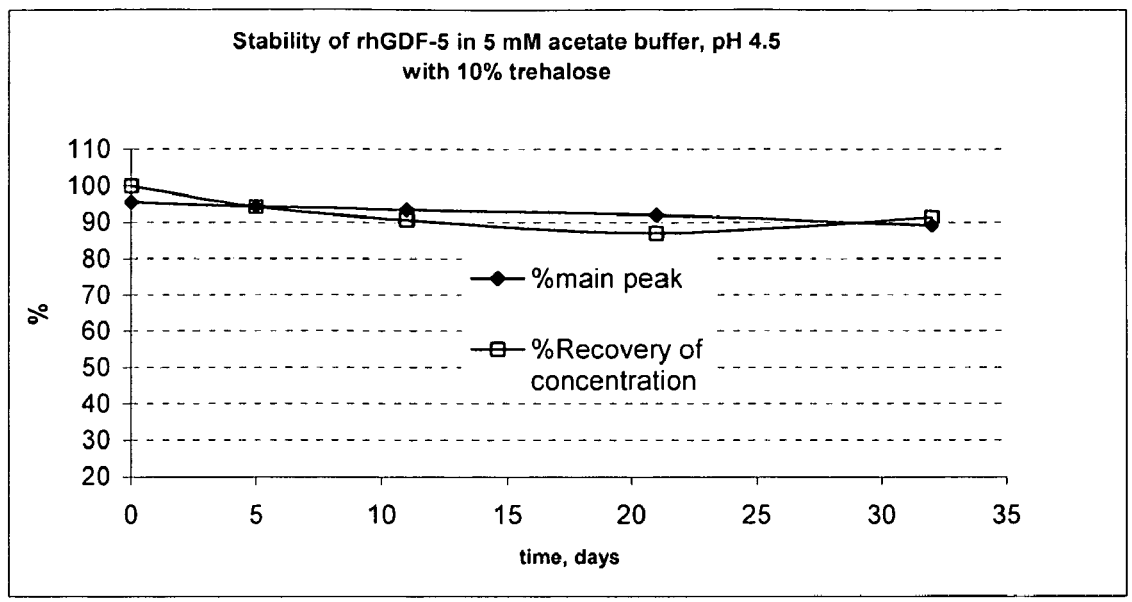
Figure 2. Stability of 0.1 mg/ml rhGDF-5 solution in 5 mM acetate buffer solution at pH 4.5 with 10% trehalose, as evidenced by HPLC.

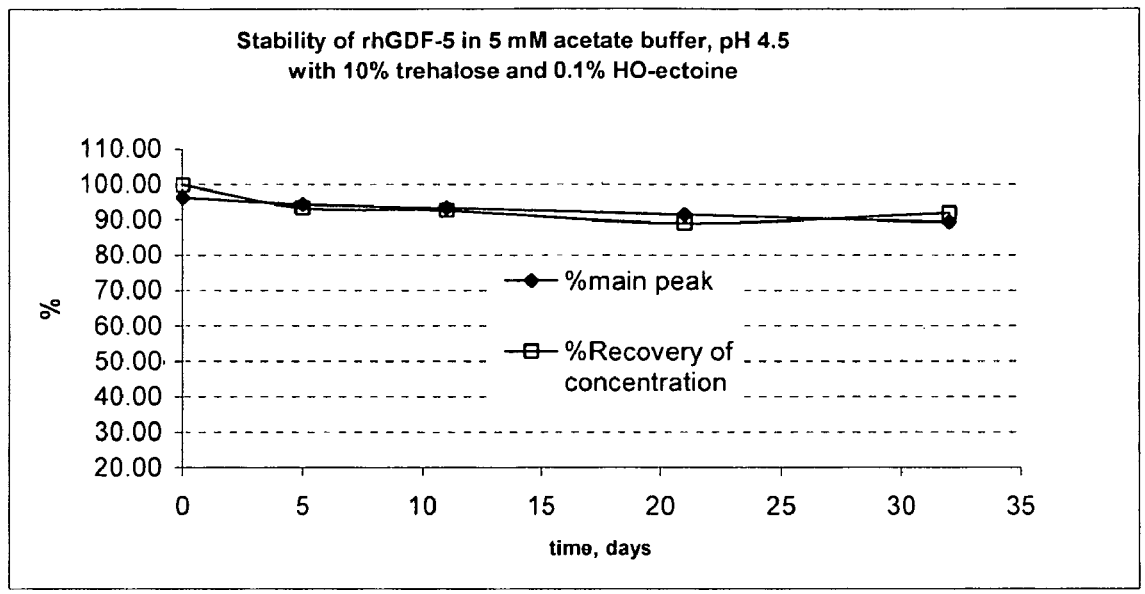
Figure 3. Stability of 0.1 mg/ml rhGDF-5 in 5 mM acetate buffer solution at pH 4.5 with 10% trehalose and 0.1% HO-ectoine after 32 days storage at 37 degrees Celsius, as evidenced by HPLC.

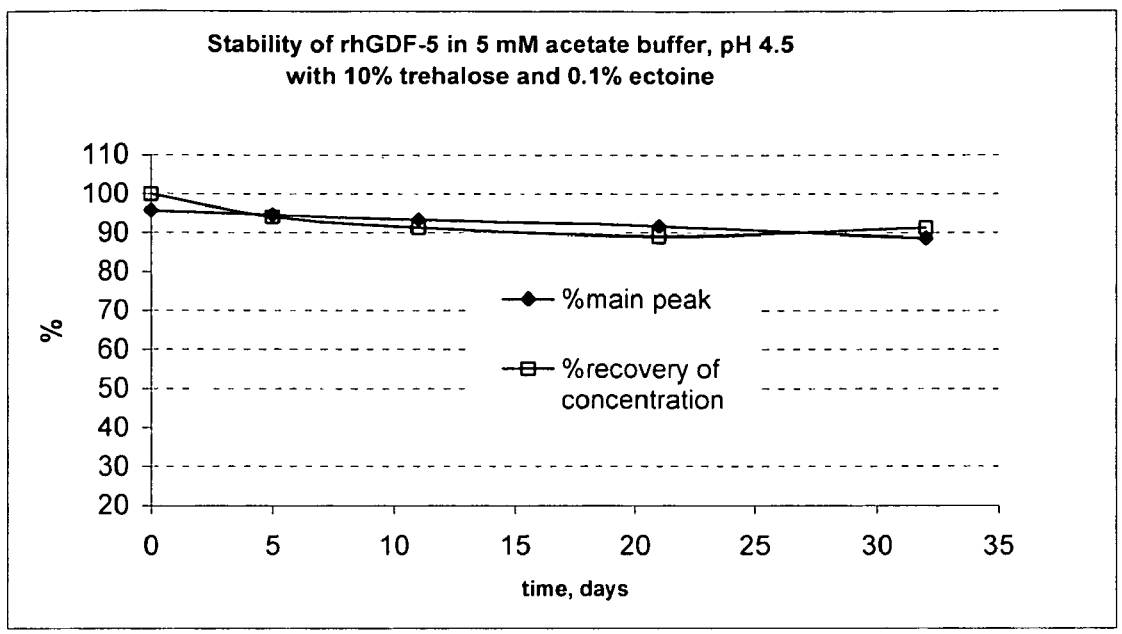
Figure 4. Stability of 0.1 mg/ml rhGDF-5 in 5 mM acetate buffer solution at pH 4.5 with 10% trehalose and 0.1% ectoine after 32 days storage at 37 degrees Celsius, as evidenced by HPLC.

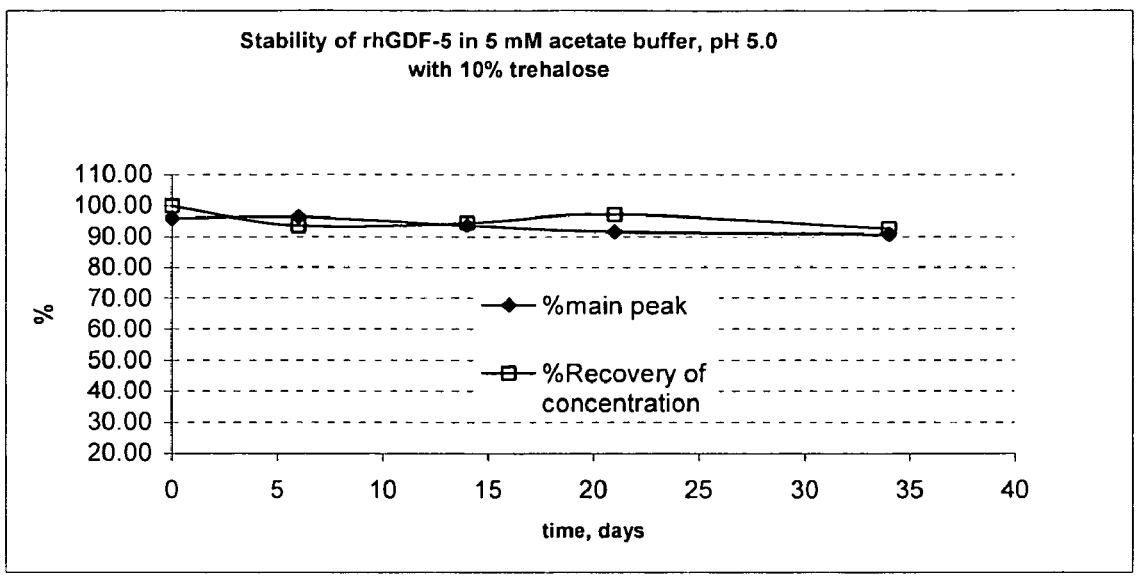
Figure 5. Stability of 0.1 mg/ml rhGDF-5 in 5 mM acetate buffer solution at pH 5.0 with 10% trehalose after 32 days storage at 37 degrees Celsius, as evidenced by HPLC.

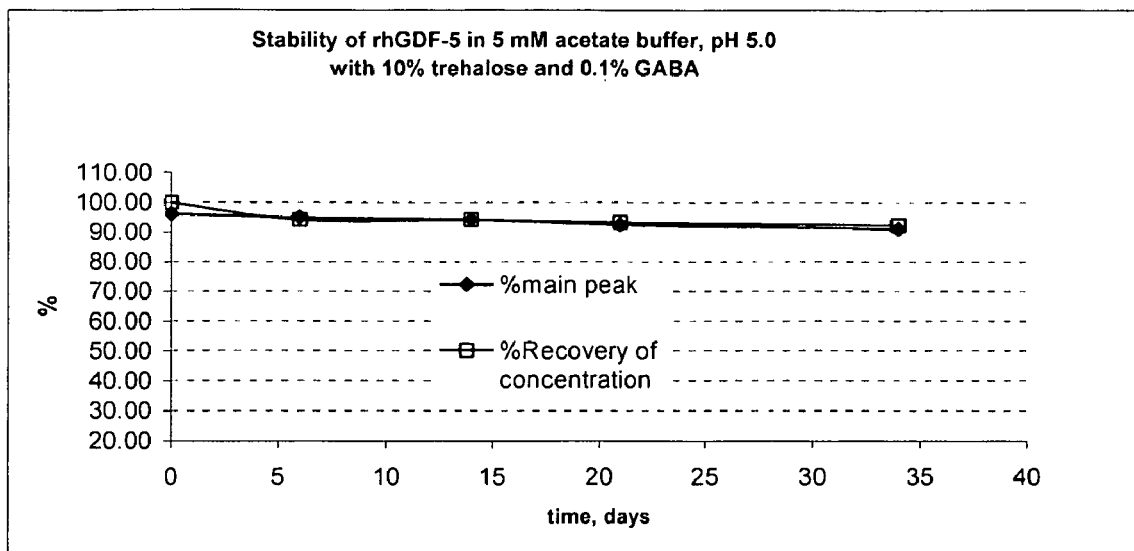
Figure 6. Stability of 0.1 mg/ml rhGDF-5 in 5 mM acetate buffer solution at pH 5.0 with 10% trehalose and 0.1% GABA after 32 days storage at 37 degrees Celsius, as evidenced by HPLC.

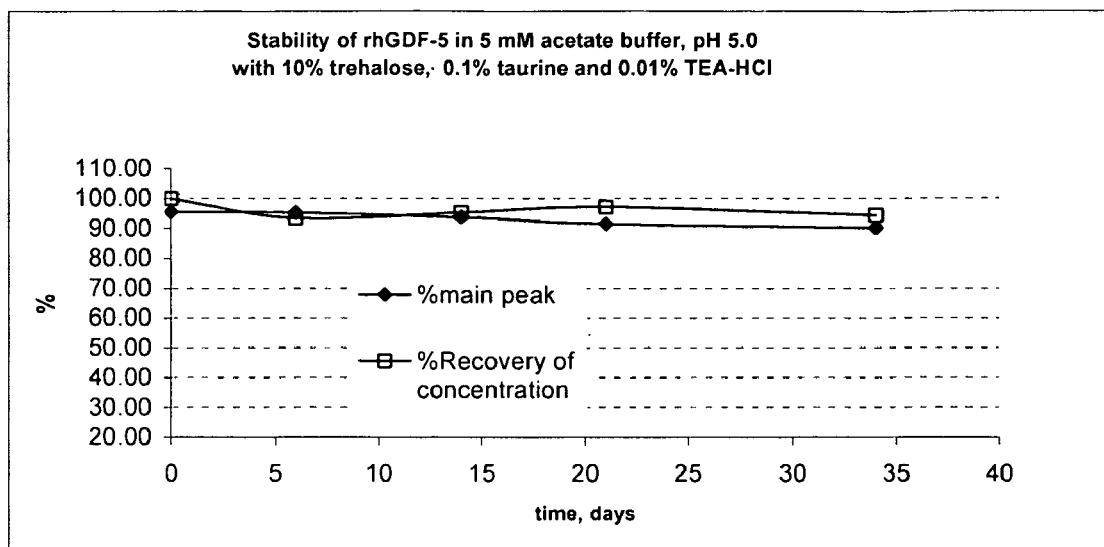
Figure 7. Stability of 0.1 mg/ml rhGDF-5 in 5 mM acetate buffer solution at pH 5.0 with 10% trehalose, 0.1% taurine and 0.01% TEA-HCl after 32 days storage at 37 degrees Celsius, as evidenced by HPLC.

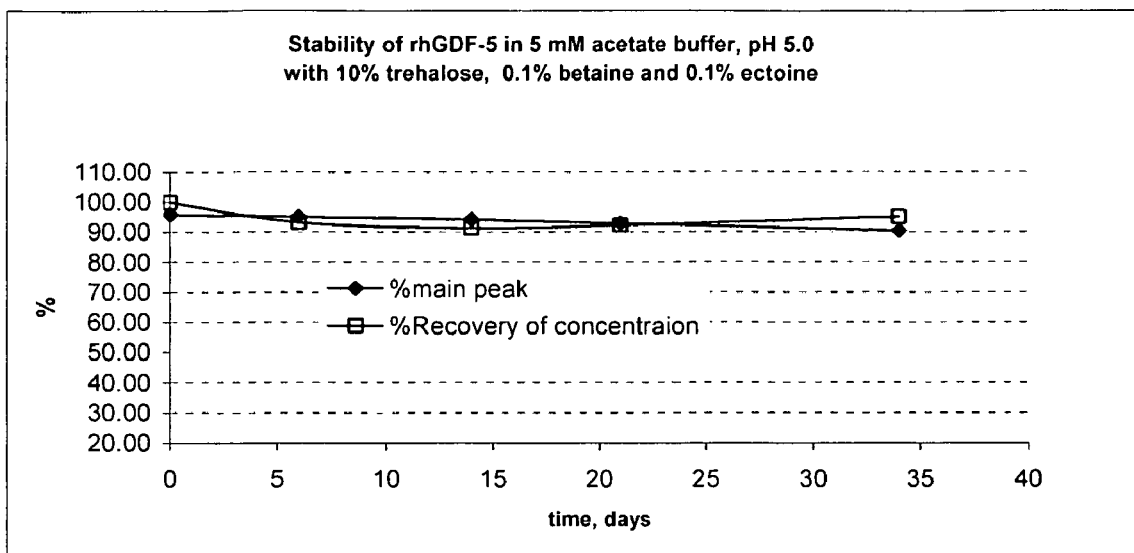
Figure 8. Stability of 0.1 mg/ml rhGDF-5 in 5 mM acetate buffer solution at pH 5.0 with 10% trehalose, 0.1% betaine and 0.1% ectoine after 32 days storage at 37 degrees Celsius, as evidenced by HPLC.

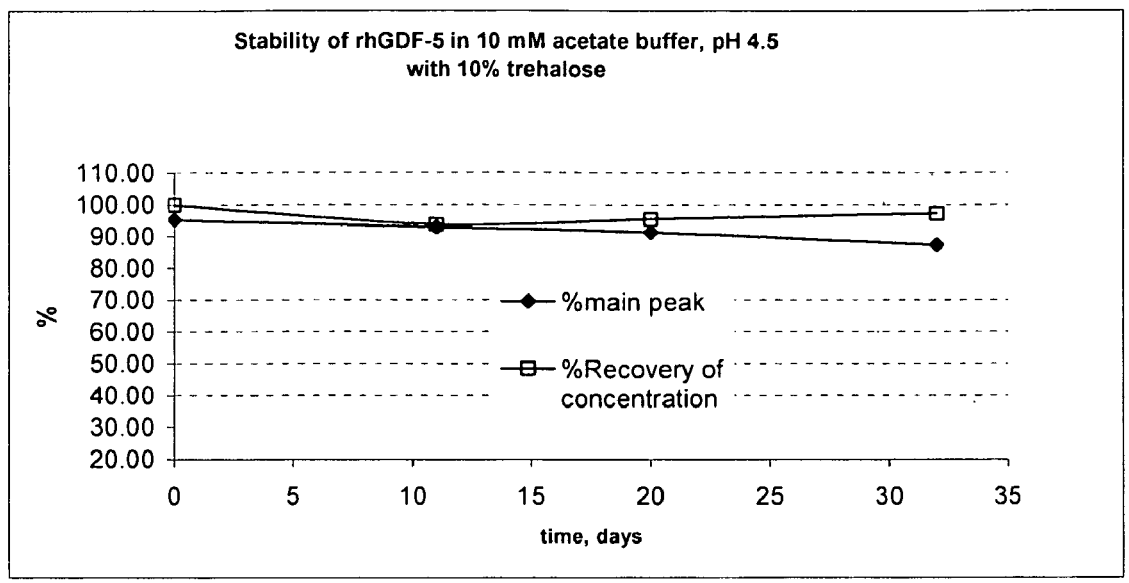
Figure 9. Stability of 0.1 mg/ml rhGDF-5 in 10 mM acetate buffer solution at pH 4.5 with 10% trehalose after 32 days storage at 37 degrees Celsius, as evidenced by HPLC.

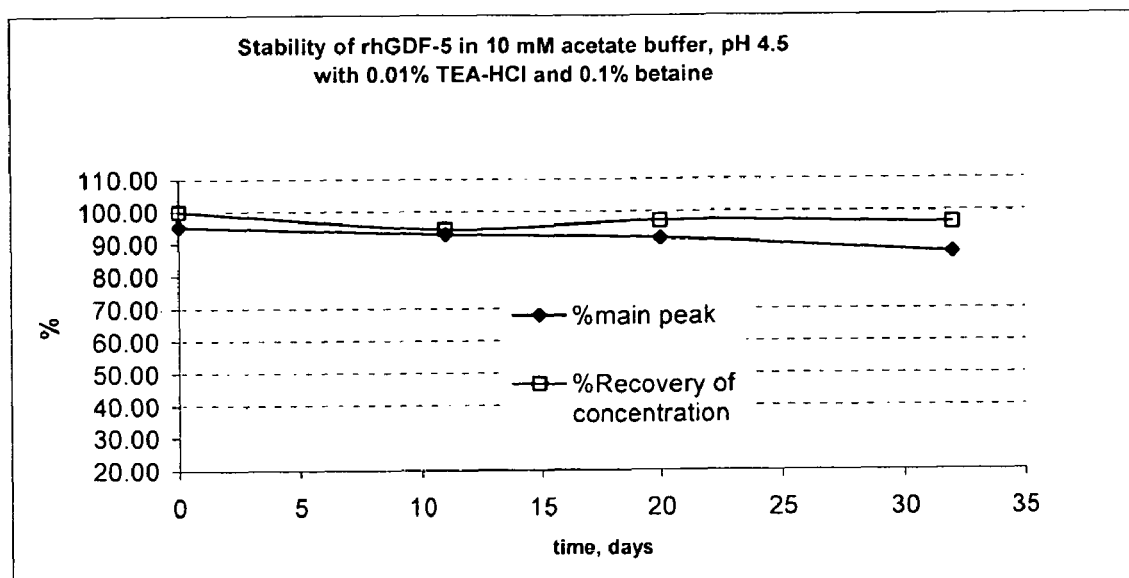
Figure 10. Stability of 0.1 mg/ml rhGDF-5 in 10 mM acetate buffer solution at pH 4.5 with 0.01% TEA-HCl and 0.1% betaine after 32 days storage at 37 degrees Celsius, as evidenced by HPLC.

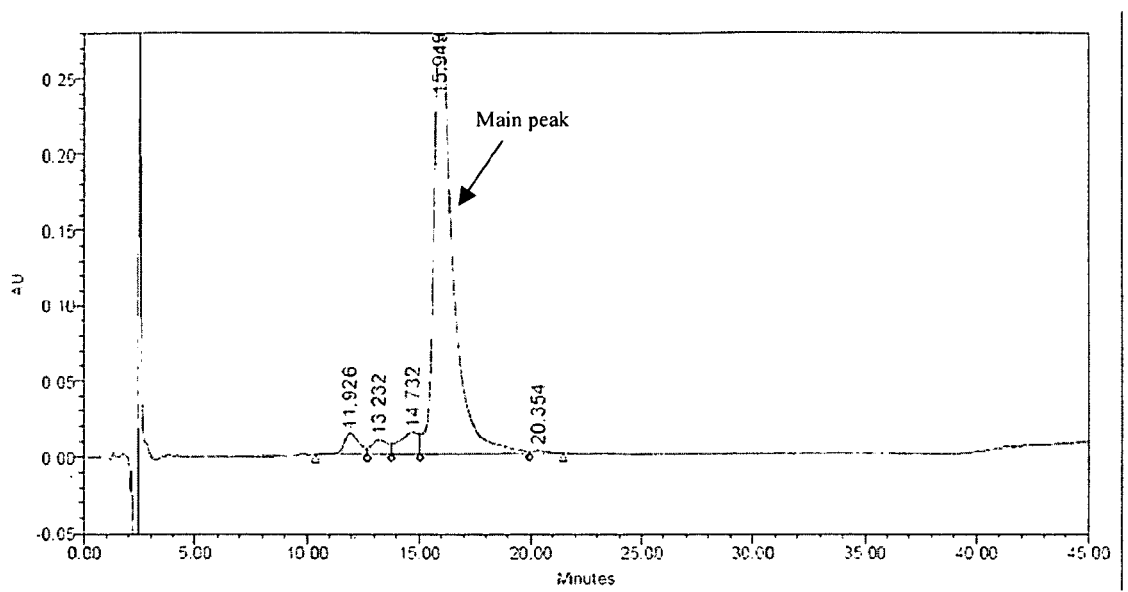
Figure 11. Stability of 0.1 mg/ml rhGDF-5 in 10 mM acetate buffer solution at pH 5 after 32 days storage at 37 degrees Celsius, as evidenced by HPLC showing 90% main peak retention and the presence of additional peaks.

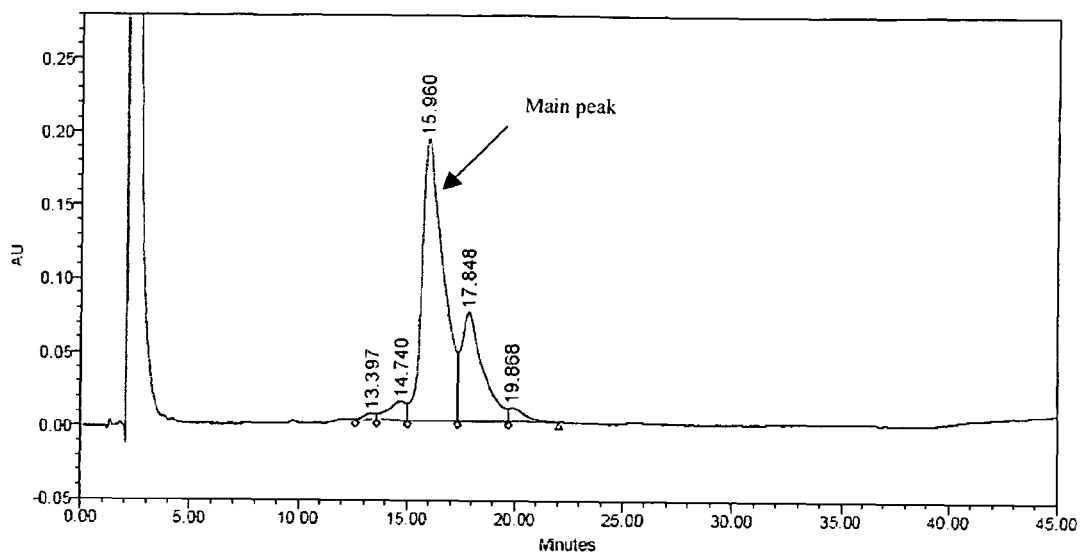
Figure 12. Degradation of 0.1 mg/ml rhGDF-5 in 5 mM maleate buffer solution at pH 4.5 with 10% trehalose after 32 days storage at 37 degrees Celsius, as evidenced by HPLC showing only 66% main peak retention and the presence of additional peaks.

LIQUID BUFFERED GDF-5 FORMULATIONS

RELATED APPLICATIONS

This application, is a non-provisional filing of a provisional application U.S. Pat. App. No. 61/044,518, filed on Apr. 14, 2008.

FIELD OF THE INVENTION

The invention relates to liquid formulations of bone morphogenetic proteins for improved stability, handling, and storage. More specifically, the invention relates to liquid formulations comprising GDF-5 in a biologically isotonic acidic solution having a pH of from about 4.0 to about 5.5, having improved protein stability during handling and delivery at body temperatures.

BACKGROUND

GDF-5 is a member of the Bone Morphogenetic Proteins (BMP), which is a subclass of the TGF-β superfamily of proteins. GDF-5 includes several variants and mutants, including mGDF-5 first isolated from the mouse by Lee (U.S. Pat. No. 5,801,014). Other variants include MP52, which is the patented name (WO 95/04819) for the human form of GDF-5, which is also known as hGDF-5 and also as LAP-4 (Triantfilou, et al. *Nature Immunology* 2, 338-345 (2001)); also CDMP-1, an allelic protein variant of hGDF-5 (WO 96/14335); also rhGDF-5, the recombinant human form manufactured in bacteria (EP 0955313); also rhGDF-5-Ala83, a monomeric variant of rhGDF-5; also BMP-14, a collective term for hGDF-5/CDMP-1 like proteins; also Radotermin, the international non-proprietary name designated by the World Health Organization; also HMW MP52's, high molecular weight protein variants of MP52; also C465A, a monomeric version wherein the cysteine residue responsible for the intermolecular cross-link is substituted with alanine; also other active monomers and single amino acid substitution mutants including N445T, L441 P, R438L, and R438K. For the purposes of this applciation the term "GDF-5" is meant to include all variants and mutants of the GDF-5 protein, and rhGDF-5 is the exemplary member having 119 amino acids.

All members of the BMP family share common structural features including a carboxy terminal active domain and share a highly conserved pattern of cysteine residues that create 3 intramolecular disulfide bonds and one intermolecular disulfide bond. The active form can be either a disulfide-bonded homodimer of a single family member or a heterodimer of two different members (see Massague, et al. *Annual Review of Cell Biology* 6:957 (1990); Sampath, et al. *Journal of Biological Chemistry* 265:13198 (1990); Celeste et al. *PNAS* 87:9843-47 (1990); U.S. Pat. No. 5,011,691, and U.S. Pat. No. 5,266,683). The proper folding of the GDF-5 protein and formation of these disulfide bonds are essential to biological functioning, and misfolding leads to inactive aggregates and cleaved fragments.

The production of BMP's from genetically modified bacteria, and of GDF-5 in particular, utilizes plasmid vectors to transform *E. coli* to produce monomer GDF-5 protein in high yield (see for example Hotten U.S. Pat. No. 6,764,994 and Makishima U.S. Pat. No. 7,235,527). The monomer is obtained from inclusion bodies, purified, and refolded into homodimers of GDF-5 protein to produce the biologically active dimer of the GDF-5 protein. The steps leading to this utilize various pharmaceutically unacceptable materials to modify the solubility in order to enable the separation and purification of the GDF-5 protein.

The degradation of proteins in general has been well described in the literature, but the storage and solubility of bone morphogenetic proteins, particularly GDF-5 has not been well described. BMP-2 is readily soluble at concentrations greater than 1 mg/ml when the pH is below 6, and above pH 6 the solubility can be increased by the addition of 1 M NaCl, 30% isopropanol, or 0.1 mM heparin (Ruppert, et al Eur J Biochem 237, 295-302 (1996). The solubility of GDF-5 is much more limited than that of BMP-2, and GDF-5 is nearly insoluble in physiological pH ranges and buffers. GDF-5 is only soluble in water at extreme pH (Honda, et al, *Journal of Bioscience and Bioengineering* 89(6), 582-589 (2000)). GDF-5 is soluble at an alkaline pH of about 9.5 to 12.0, however proteins degrade quickly under these conditions and thus acidic conditions are used for preparation of GDF-5 protein.

The use of bone morphogenetic proteins has been well described in the case of BMP-2 and the growth of bone. GDF-5 has more activity in other areas of musculoskeletal development than BMP-2, and indeed in other areas of cellular biochemistry and regulation. The use of GDF-5 in these other areas presents fertile ground for potential treatments of various diseases and medical conditions. A major challenge for storage, handling, and delivery to target tissues is the stability of the GDF-5 protein molecule. Bulk GDF-5 protein is typically stored at sub-zero temperatures and lyophilized products are stored at 2-8C to protect the protein from degradation, but liquid formulations are required for many uses, including delivering liquid product in an implantable drug delivery pump.

In the past we have shown that a high amount of excipient, such as 60% trehalose, could be used to protect the GDF-5 protein at body temperature for extended periods of time. These formulas however were not isotonic and must be diluted before reaching the injection site. Biocompatible formulations of the GDF-5 protein present great challenges to obtain reasonable solubility and concurrent stability of the GDF-5 protein. Thus there is a need for improved formulations for the storage, handling, and delivery of GDF-5 protein solutions.

SUMMARY OF THE INVENTION

The present invention is directed to formulations of buffered isotonic GDF-5 protein solutions having improved storage and handling properties at body temperatures, providing for stability of the GDF-5 protein molecule. A preferred embodiment of the invention includes 0.1 mg/ml rhGDF-5 in a 5-10 mM acetate buffer at pH 4.5 -5 with 10% trehalose as an excipient, providing approximately 90% retention of the GDF-5 protein after 32 days storage at 37 degrees Celsius.

BRIEF DESCRIPTION OF THE FIGURES

FIG. 1 shows the stability of 0.1 mg/ml rhGDF-5 in 5 mM acetate buffer solution at pH 4.5 after 32 days storage at 37 degrees Celsius, as evidenced by HPLC.

FIG. 2 shows the stability of 0.1 mg/ml rhGDF-5 solution in 5 mM acetate buffer solution at pH 4.5 with 10% trehalose, as evidenced by HPLC.

FIG. 3 shows the stability of 0.1 mg/ml rhGDF-5 in 5 mM acetate buffer solution at pH 4.5 with 10% trehalose and 0.1% HO-ectoine after 32 days storage at 37 degrees Celsius, as evidenced by HPLC.

FIG. 4 shows the stability of 0.1 mg/ml rhGDF-5 in 5 mM acetate buffer solution at pH 4.5 with 10% trehalose and 0.1% ectoine after 32 days storage at 37 degrees Celsius, as evidenced by HPLC.

FIG. 5 shows the stability of 0.1 mg/ml rhGDF-5 in 5 mM acetate buffer solution at pH 5.0 with 10% trehalose after 32 days storage at 37 degrees Celsius, as evidenced by HPLC.

FIG. 6 shows the stability of 0.1 mg/ml rhGDF-5 in 5 mM acetate buffer solution at pH 5.0 with 10% trehalose and 0.1% GABA after 32 days storage at 37 degrees Celsius, as evidenced by HPLC.

FIG. 7 shows the stability of 0.1 mg/ml rhGDF-5 in 5 mM acetate buffer solution at pH 5.0 with 10% trehalose, 0.1% taurine and 0.01% TEA-HCI after 32 days storage at 37 degrees Celsius, as evidenced by HPLC.

FIG. 8 shows the stability of 0.1 mg/ml rhGDF-5 in 5 mM acetate buffer solution at pH 5.0 with 10% trehalose, 0.1% betaine, and 0.1% ectoine after 32 days storage at 37 degrees Celsius, as evidenced by HPLC.

FIG. 9 shows the stability of 0.1 mg/ml rhGDF-5 in 10 mM acetate buffer solution at pH 4.5 with 10% trehalose after 32 days storage at 37 degrees Celsius, as evidenced by HPLC.

FIG. 10 shows the stability of 0.1 mg/ml rhGDF-5 in 10 mM acetate buffer solution at pH 4.5 with 0.01% TEA-HCI and 0.1% betaine after 32 days storage at 37 degrees Celsius, as evidenced by HPLC.

FIG. 11 shows an HPLC chromatogram depicting the stability of 0.1 mg/ml rhGDF-5 in 10 mM acetate buffer solution at pH 5 with 10% trehalose 32 days storage at 37 degrees Celsius, as evidenced by 90% main peak retention.

FIG. 12 shows an HPLC chromatogram depicting the degradation of 0.1 mg/ml rhGDF-5 in 5 mM maleate buffer solution at pH 4.5 with 10% trehalose after 32 days storage at 37 degrees Celsius, as evidenced by <70% main peak retention.

DETAILED DESCRIPTION OF THE INVENTION

For the purposes of this application the definitions of the following terms will be useful to clearly and concisely point out the subject matter of the claimed invention. The term "Growth and Differentiation Factor 5" (herein referred to as "GDF-5") as used herein is understood to include all synonyms, variants and mutations of the GDF-5 protein molecule, including, but not limited to GDF-5, mGDF-5, hGDF-5, MP-52, LAP-4, radotermin, CDMP-1, C465A, and rhGDF-5, wherein rhGDF-5 is the exemplary member of the group. It is also understood to include monomeric GDF-5 proteins, which have also been shown to be biologically active.

The term "room temperature", herein abbreviated as "RT" or "R.T.", is understood to mean the ambient temperature of an ordinary office or laboratory, being from about 18 to about 25 degrees Celsius. The term "body temperature" as used herein is understood to mean the average body temperature of a mammal, being from about 34 to about 40 degrees Celsius, and generally accepted to be about 37 degrees Celsius for humans.

The term "bulk" as used herein when referring to "bulk protein" or "bulk solution" is understood to mean a purified solution of GDF-5 in from about 1 to about 10 mM HCl and stored at about −80 degrees Celsius, and is equivalent with the terms "stock", "stock protein", and "stock solution".

The term "buffer" is understood to have its common meanings in the literature, that as a noun being an acid and conjugate base pair capable of providing a liquid with the capacity to maintain a stable pH upon the addition of acid or base, and the term "buffer" as a verb is understood to describe the action of maintaining the pH of a solution by the addition of a buffer. Exemplary buffer conjugate bases include, but are not limited to, acetate, lactate, tartarate, maleate, citrate, and combinations thereof, wherein acetate is the exemplary member of the group.

The terms "isotonic", "isotonicity", and "biological isotonicity" as used herein have their common meanings in the literature and refer to a solution being or having an osmolarity equivalent to that of human blood plasma, and is about 290 mosm/L with a range of about +/−20 mosm/L.

The term "excipient" as used herein is understood to mean any extra ingredient or additive other than a buffer that is added to a protein composition. Exemplary excipients include trehalose, sucrose, raffinose, glucose, mannitol, TMAO, TEA-HCl, taurine, β-alanine, betaine, ectoine, HO-ectoine, GABA, and combinations thereof.

The term "TMAO" as used herein is understood to mean trimethylamineoxide; the term "TEA-HCl" as used herein is understood to mean triethylaminehydrochloride; the term "GABA" as used herein is understood to mean gamma-amino butyric acid.

The term "tonicity adjuster" as used herein is understood to mean a solute that is added to a protein solution for the purpose of making the solution isotonic. The solute may also have other chemical or biological properties in addition to modifying the tonicity of the solution. Exemplary tonicity adjusters include salts, such as NaCl, and certain carbohydrates, including but not limited to trehalose, sucrose, raffinose, glucose, and mannitol. Note that these tonicity adjusters may also be considered excipients, however not all excipients are useful as tonicity adjusters. The amount of some excipients that would need to be added in order to affect tonicity would create other undesirable effects and thus negate their utility as a tonicity adjuster. However, in very small quantities these other excipient materials provide useful and desirable properties without substantially affecting the tonicity of the solution.

The term "HPLC" as used herein is understood to have its common meaning of High Pressure Liquid Chromatography, also known as High Performance Liquid Chromatography, and also includes the terms "reversed phase HPLC" or "rp-HPLC".

Since it's discovery and the subsequent development of recombinant human forms, GDF-5 has been stored in a 10 mM HCl solvent system at −80 degrees Celsius to preserve the GDF-5 protein structure. GDF-5 is less soluble than other BMP's, including BMP-2, for which the bulk of the scientific literature is directed to. There are few reports, if any, available on the solubility and stability of GDF-5. The preparation and isolation of GDF-5 monomer protein and the subsequent refolding into dimer presents a separate set of issues and problems than that of the handling and storage of the bioactive dimer. Working with the mature dimer GDF-5 protein in biocompatible formulations presents a different set of problems, and the literature yields very little physicochemical information regarding the solubility and stability of the GDF-5 dimer protein.

The broad spectrum of activity of GDF-5 in musculoskeletal development and also the expression of GDF-5 receptors in various tissues presents significant opportunities for therapies and treatment. One major drawback to using GDF-5 for treatment is the fragile nature of the protein. We have investigated the use of a number of different buffer systems and excipients in order to improve the stability of GDF-5 protein solutions during storage, handling, and delivery, and herein describe useful formulations for working with this protein.

In the past we have shown that a high amount of excipient, such as 60% trehalose, could be used to protect the GDF-5 protein at body temperature for extended periods of time. These formulas however were not isotonic, and required dilution before use. Additionally, these solutions were quite viscous and were potentially problematic to handle.

We undertook several studies of various GDF-5 solutions to investigate buffer systems and excipients for the improved storage and handling of GDF-5 protein solutions having biological isotonicity and stability, particularly at body temperature. The stability of the GDF-5 protein was determined by reversed phase HPLC (herein referred to simply as "HPLC"), and the percent retention of the main peak was used as a measure of the stability or degradation of the GDF-5 protein. Our past results have shown that this is a reliable method of determining the stability of the GDF-5 protein molecule, and degradation of the GDF-5 protein is readily observed by the reduction of the main peak and the appearance of extraneous peaks due to oxidation, deamidation, aggregation, cleavage and fragmentation. These results were also confirmed in the present experiments.

For example, FIG. 11 shows an HPLC chromatogram of 0.1 mg/ml rhGDF-5 in 10 mM acetate buffer solution at pH 5.0 after 32 days storage at 37 degrees Celsius, showing 90% main peak retention and also the presence of minor additional peaks. In contrast, FIG. 12 shows the degradation of 0.1 mg/ml rhGDF-5 in 5 mM maleate buffer solution at pH 4.5 with 10% trehalose after 32 days storage at 37 degrees Celsius, showing only 66% main peak retention and the presence of additional peaks. We also evaluated the solutions based on the visual clarity of the solutions, with a hazy or cloudy solution being evidence of poor solubility and/or aggregation of the GDF-5 protein.

Numerous compounds have been shown to be useful in other protein formulations, including buffer systems of acetate, lactate, maleate, citrate, succinate, phosphate, and tartrate, and other excipients such as trehalose, mannitol, sucrose, raffinose, trimethylamine oxide, trimethylamine hydrochloride, triethylamine hydrochloride, beta-alanine, alanine, glycine, taurine, betaine, ectoine, HO-ectoine, L-proline, potassium aspartate, sodium aspartate, heat shock protein, dextran, cyclodextrans, glycine, arginine, PEGs, pluronics, lipids, phospholipids, diacylglyecerols, vitamin E-acetate, and PEG-vitamin E succinate. However, there is no known evidence or literature of the use or benefit of these excipients with GDF-5.

Our experiments were designed to be isotonic solutions with the goal of still maintaining the solubility and stability of the GDF-5 protein molecule. A GDF-5 protein concentration of 0.1 mg/ml was used for all experiments. The results showed that a 5 mM acetate buffer solution at pH 4.5 could be used to maintain a clear liquid that showed approximately 90% retention (stability) of the GDF-5 protein HPLC main peak after 32 days storage at 37 degrees Celsius (see FIG. 1).

The addition of other excipients did not enhance or detract from the GDF-5 protein stability under the experimental conditions studied, but these additional excipients may provide other benefits under other conditions. Thus, the addition of up to 0.2%, or possibly even up to about 0.5% of these other excipients may have little affect on the stability of the protein under the present study conditions, but may enhance the solubility or stability of the protein under other conditions. Increasing the pH of the acetate buffer to 5.0 did not detract from the stability of the GDF-5 protein (see table 2). Thus, a formulation of 5 mM acetate buffer at a pH of from about 4.2 to about 5.3 with 10% trehalose added to adjust the tonicity and one or more excipients at 0.1 wt. % of taurine, betaine, b-alanine, TMAO, GABA, ectoine, HO-ectoine, 0.01 wt. % of TMAO or TEA-HCl, and various combinations thereof provided for protection of the GDF-5 protein after 32 days storage at 37 degrees Celsius (See table 1 &2, and also FIGS. 1-8).

We then tested a similar series of formulations and excipients at pH 5.5, however all of these samples were hazy, indicating poor solubility and/or aggregation of the GDF-5 protein (see table 3). No HPLC scans were performed on these samples.

We also tested the stability of the 0.1 mg/ml GDF-5 protein solution in several 5 mM glycine-HCl buffers ranging from pH 3.9 to 5.0. The samples were tested with and without 10% trehalose to adjust the tonicity, and also with various combinations of the excipients taurine, betaine, b-alanine, and TEA-HCl. All of these samples yielded hazy solutions (see table 4), and were not further tested by HPLC. Similarly, we also tested the stability of the 0.1 mg/ml GDF-5 protein solution in other buffer systems, including a 5 mM citrate buffer at pH 4.4 with 10% trehalose, a 0.25 mM HCl solution at pH 3.5 with 10% trehalose, and a 0.25 mM HCl solution at pH 3.5 without trehalose. All of these solutions were also hazy, indicating poor solubility and/or aggregation of the GDF-5 protein, and no HPLC scans were performed on these samples (see table 4). Thus, it is surprising that an acetate buffer system at higher pH can provide superior solubility and protection of the GDF-5 protein molecule than other commonly known buffers used for biocompatible formulations at a lower pH, when lower pH is known to enhance the stability of GDF-5.

We then further tested the stability of the 0.1 mg/ml GDF-5 protein solution in a 10 mM acetate buffer system at pH 4.5 and also at pH 5.0 with selected combinations of excipients. All of these solutions were clear, and subsequent testing after storage at 37 degrees Celsius showed that these formulations afforded protection of the GDF-5 protein molecule, as evidenced by retention of approximately 85% of the main peak after 32 days storage at 37 degrees Celsius (see tables 5 & 6). Further testing in 10 mM acetate buffer at pH 5.0 with 10% sucrose instead of trehalose added as a tonicity adjuster, and with various other excipients added also gave positive results, yielding nearly 90% retention of the main peak by HPLC (see table 7).

Although many of the excipients and combinations of excipients tested did not exhibit superior results under the study conditions of time, temperature, pH, and osmolality tested, they also did not exhibit detrimental effects upon the GDF-5 protein stability. Thus, they may show benefits in other systems, methods, or conditions, such as in a specific biological tissue, organ, or cell type, or over a longer time period or at other temperatures.

It is an object of the present invention to provide a formulation of GDF-5 protein in a biocompatible buffer system that provides for improved protein stability during handling and storage at body temperature, as evidenced by the retention of at least 80% of the HPLC main peak. It is another object of the present invention to provide an isotonic solution of GDF-5 protein that is stable during storage and handling at body temperature, as evidenced by the retention of at least 80% of the HPLC main peak. It is another object of the present invention to provide an isotonic solution of GDF-5 protein having an acetate buffer with a pH of from about 4.2 to about 5.3, and further having 10 weight percent of a tonicity adjuster selected from the group consisting of trehalose, sucrose, raffinose, glucose, mannitol, and combinations thereof, that is stable during storage and handling at body temperature, as evidenced by the retention of at least 80% of the HPLC main peak.

It is another object of the present invention to provide a method of preserving a solution of GDF-5 protein by providing an acetate buffered solvent system having biological isotonicity and a pH of from about 4.2 to about 5.3, wherein the GDF-5 protein is stabilized during handling and storage at body temperature up to and including 37 degrees Celsius for up to 32 days, as evidenced by the retention of at least 80% of the HPLC main peak.

The following examples are meant only to be illustrative in nature of the present invention, and not to be limiting in scope. One skilled in the art would easily conceive of other embodiments that would be considered within the scope of the present invention.

EXAMPLE 1

Bulk frozen rhGDF-5 protein solution was thawed overnight. A portion of the stock solution was used in a 5 mM acetate buffer at pH 4.5 and tested with 10% trehalose to adjust the tonicity of the solution to be isotonic and various other excipients to evaluate the stability of the GDF-5 protein as evidenced by the clarity of the solution and by HPLC analysis of the main peak. Data were collected after 5, 11, 22, and 32 days storage at 37 degrees Celsius. Control samples having buffer only and buffer plus 10% trehalose were included in the experiment. The results are shown below in table 1. Surprisingly, the buffer alone provided nearly equivalent protection of the GDF-5 protein as compared with the other samples. None of the other excipients tested showed any noticeable improvement or reduction of the stability of the GDF-5 protein. FIG. 1 shows a graph of the HPLC main peak % and the % recovery of concentration of the control sample with acetate buffer at pH 4.5 alone, showing approximately 90% retention (stability) of the GDF-5 protein after 5, 11, 22, and 32 days at 37 degrees Celsius. FIG. 2 shows a similar graph of the HPLC main peak % and the % recovery of concentration of the sample with acetate buffer at pH 4.5 plus 10% trehalose, also showing approximately 90% retention of the GDF-5 protein after 32 days at 37 degrees Celsius. FIGS. 3 and 4 show similar graphs of the HPLC main peak % and the % recovery of concentration of the samples with 10% trehalose plus 0.1% HO-ectoine or 0.1% ectoine, respectively, also showing approximately 90% retention of the GDF-5 protein after 32 days at 37 degrees Celsius. See table 1 below for a complete listing of the various combinations of excipients tested and the results obtained. Note that all of the values are nearly equivalent, showing that the acetate buffer at pH 4.5 is able to maintain the stability of the GDF-5 protein at about 90%, with or without the addition of other excipients.

TABLE 1

Data showing the stability of 0.1 mg/mL rhGDF-5 in 5 mM acetate buffer at pH 4.5, also tested with 10% trehalose and other excipients.

| Sample ID | Other Excipients | pH | Clarity | HPLC Analysis, % main peak | | | | |
|---|---|---|---|---|---|---|---|---|
| | | | | Time 0 | Day 5 | Day 11 | Day 22 | Day 32 |
| RR303LN-73-56 | 0.01% TMAO | 4.4 | Clear | 96.35 | 94.56 | 93.58 | 91.90 | 89.25 |
| RR303LN-73-57 | 0.1% ectoine | 4.3 | Clear | 95.83 | 94.68 | 93.41 | 91.73 | 88.67 |
| RR303LN-73-58 | 0.01% TMAO/0.1% ectoine | 4.4 | Clear | 95.92 | 95.88 | 93.49 | 91.87 | 88.98 |
| RR303LN-73-59 | 0.1% HO-ectoine | 4.3 | Clear | 96.27 | 94.42 | 93.42 | 91.54 | 89.35 |
| RR303LN-73-60 | 0.01% TMAO/0.1% HO-ectoine | 4.4 | Clear | 96.16 | 95.68 | 93.59 | 91.64 | 89.32 |
| RR303LN-73-61 | 0.1% taurine/0.1% betaine | 4.3 | Clear | 96.07 | 94.39 | 93.21 | 91.15 | 89.68 |
| RR303LN-73-62 | 0.1% taurine/0.1% ectoine | 4.3 | Clear | 95.53 | 94.65 | 92.96 | 90.95 | 88.96 |
| RR303LN-73-63 | 0.15 taurine/0.1% HO-ectoine | 4.3 | Clear | 95.82 | 94.73 | 93.33 | 91.25 | 89.00 |
| RR303LN-73-64 | 0.1% taurine/0.01% TEA-HCl | 4.3 | Clear | 95.81 | 94.72 | 93.11 | 91.39 | 89.51 |
| RR303LN-73-65 | 0.1% taurine/0.1% b-alanine | 4.6 | Clear | 96.36 | 95.00 | 93.54 | 91.36 | 89.30 |
| RR303LN-73-66 | 0.01% TMAO/0.1% taurine | 4.4 | Clear | 95.21 | 94.42 | 93.15 | 91.56 | 89.09 |
| RR303LN-73-67 | 0.01% TEA-HCl/0.1% b-alanine | 4.6 | Clear | 96.14 | 94.76 | 93.51 | 91.73 | 89.34 |
| RR303LN-73-68 | 0.01% TEA-HCl/0.1% betaine | 4.3 | Clear | 95.23 | 93.70 | 93.30 | 91.84 | 89.50 |
| RR303LN-73-69 | 0.1% b-alanine/0.1% betaine | 4.6 | Clear | 96.49 | 94.18 | 93.17 | 91.67 | 89.07 |
| RR303LN-73-70 | 0.1% b-alanine/0.1% ectoine | 4.6 | Clear | 96.12 | 94.47 | 93.34 | 91.31 | 88.54 |
| RR303LN-73-71 | 0.1% b-alanine/0.1% HO-ectoine | 4.6 | Clear | 95.63 | 95.05 | 93.59 | 91.55 | 89.23 |
| RR303LN-73-72 | 0.1% betaine/0.1% ectoine | 4.3 | Clear | 95.72 | 94.01 | 93.18 | 91.08 | 88.55 |
| RR303LN-73-73 | 10% trehalose only | 4.3 | Clear | 96.09 | 94.93 | 93.57 | 91.89 | 89.26 |
| RR303LN-73-74 | No trehalose or other excipients | 4.3 | Clear | 95.52 | 94.33 | 93.51 | 92.06 | 89.09 |

EXAMPLE 2

In this experiment rhGDF-5 was also formulated at approximately 0.1 mg/mL in 5 mM acetate buffer, but at pH 5.0 instead of pH 4.5 as in example 1. 10% trehalose was added to adjust the tonicity, and various other excipients were added as indicated in table 2. These formulations were also stable at 37 degrees Celsius for 32 days as shown in table 2. FIG. 5 shows a graph of the HPLC main peak % and the % recovery of concentration of the sample having 5 mM acetate buffer at pH 5.0 and 10% trehalose, showing approximately 90% retention of the GDF-5 protein after 32 days storage at 37 degrees Celsius. FIG. 6 shows a graph of the HPLC main peak % and the % recovery of concentration of the sample having acetate buffer at pH 5.0 and 10% trehalose with 0.1% GABA, also showing approximately 90% retention of the GDF-5 protein after 32 days storage at 37 degrees Celsius. FIG. 7 shows a graph of the HPLC main peak % and the % recovery of concentration of the sample having acetate buffer at pH 5.0 and 10% trehalose with 0.1% taurine and 0.01% TEA-HCl, also showing approximately 90% retention of the GDF-5 protein after 32 days storage at 37 degrees Celsius. FIG. 8 shows a graph of the HPLC main peak % and the % recovery of concentration of the sample having acetate buffer at pH 5.0 with 10% trehalose, 0.1% betaine, and 0.1% ectoine, also showing approximately 90% retention of the GDF-5 protein after 32 days storage at 37 degrees Celsius.

TABLE 2

Stability of 0.1 mg/mL rhGDF-5 in 5 mM Acetate buffer at pH 5.0, also tested with 10% trehalose and other excipients.

| Sample ID | Other excipients | pH | Clarity | HPLC Analysis, % main peak | | | | |
|---|---|---|---|---|---|---|---|---|
| | | | | Time 0 | Day 6 | Day 14 | Day 21 | Day 34 |
| RR303LN-76-75 | 0.01% TMAO | 4.9 | Clear | 96.43 | 96.14 | 95.45 | 93.15 | 92.35 |
| RR303LN-76-76 | 0.1% ectoine | 4.8 | Clear | 96.42 | 95.50 | 94.59 | 93.13 | 90.15 |
| RR303LN-76-77 | 0.01% TMAO/0.1% ectoine | 5.0 | Clear | 95.86 | 95.50 | 94.68 | 92.97 | 91.04 |
| RR303LN-76-78 | 0.1% GABA | 5.1 | Clear | 96.17 | 95.00 | 94.36 | 92.57 | 91.09 |
| RR303LN-76-79 | 0.01% TMAO/0.1% GABA | 5.2 | Clear | 95.41 | 95.84 | 94.30 | 93.09 | 91.21 |
| RR303LN-76-80 | 0.1% taurine/0.1% betaine | 4.8 | Clear | 95.63 | 95.95 | 94.16 | 92.50 | 90.28 |
| RR303LN-76-81 | 0.1% taurine/0.1% ectoine | 4.9 | Clear | 95.94 | 95.93 | 94.15 | 92.34 | 90.22 |
| RR303LN-76-82 | 0.15 taurine/0.1% GABA | 5.1 | Clear | 96.34 | 95.63 | 94.74 | 92.02 | 91.01 |
| RR303LN-76-83 | 0.1% taurine/0.01% TEA-HCl | 4.8 | Clear | 95.59 | 95.22 | 93.81 | 91.56 | 90.15 |
| RR303LN-76-84 | 0.1% taurine/0.1% b-alanine | 5.0 | Clear | 95.85 | 94.95 | 94.38 | 91.18 | 90.33 |
| RR303LN-76-85 | 0.01% TMAO/0.1% taurine | 4.9 | Clear | 95.81 | 94.14 | 93.96 | 91.84 | 91.09 |
| RR303LN-76-86 | 0.01% TEA-HCl/0.1% b-alanine | 5.0 | Clear | 95.44 | 96.16 | 93.80 | 91.90 | 90.18 |
| RR303LN-76-87 | 0.01% TEA-HCl/0.1% betaine | 4.8 | Clear | 95.99 | 95.82 | 93.54 | 91.88 | 90.47 |
| RR303LN-76-88 | 0.1% b-alanine/0.1% betaine | 5.0 | Clear | 95.58 | 95.72 | 94.49 | 91.61 | 90.74 |
| RR303LN-76-89 | 0.1% b-alanine/0.1% ectoine | 5.0 | Clear | 95.27 | 95.46 | 94.50 | 92.39 | 90.39 |
| RR303LN-76-90 | 0.1% b-alanine/0.1% GABA | 5.2 | Clear | 95.48 | 95.88 | 93.89 | 91.51 | 91.24 |
| RR303LN-76-91 | 0.1% betaine/0.1% ectoine | 4.8 | Clear | 95.93 | 95.16 | 94.27 | 92.98 | 90.44 |
| RR303LN-76-92 | 10% trehalose only | 4.8 | Clear | 95.90 | 96.33 | 93.60 | 91.61 | 90.74 |

EXAMPLE 3

Similar to examples 1 and 2, rhGDF-5 was formulated at 0.1 mg/mL in 5 mM acetate buffer at pH 5.5 with 10% trehalose and other excipients, and all of these protein solutions all hazy (see table 3). Additionally, 5 mM citrate buffer at pH 4.5, glycine-HCl buffer at pH 4.5, and 0.25 mM HCl solvents were also evaluated. These formulations were also observed to be hazy, as shown in table 4.

TABLE 3

Stability of 0.1 mg/mL rhGDF-5 in 5 mM acetate buffer at pH 5.5, and also with 10% trehalose and other excipients.

| Sample ID | Other Excipients | pH | Clarity | HPLC Analysis, % main peak | | | |
|---|---|---|---|---|---|---|---|
| | | | | Time 0 | Day 11 | Day 20 | Day 32 |
| RR303LN-79-98 | 10% trehalose only | 5.3 | Hazy | NA | NA | NA | NA |
| RR303LN-79-99 | 0.1% taurine/0.1% betaine | 5.3 | Hazy | NA | NA | NA | NA |
| RR303LN-79-100 | 0.1% taurine/0.1% b-alanine | 5.4 | Hazy | NA | NA | NA | NA |
| RR303LN-79-101 | 0.01% TEA-HCl/0.1% b-alanine | 5.4 | Hazy | NA | NA | NA | NA |
| RR303LN-79-102 | 0.01% TEA-HCl/0.1% betaine | 5.3 | Hazy | NA | NA | NA | NA |

EXAMPLE 4 rhGDF-5 was formulated at 0.1 mg/mL in glycine and citrate buffers at various pH with 10% trehalose and other excipients, and all of these protein solutions were hazy (see table 4).

TABLE 4

Stability of 0.1 mg/mL rhGDF-5 in various buffers with 10% trehalose and other excipients.

| Sample ID | Other Excipients | pH | Buffer | Clarity | HPLC Analysis, % main peak | | | |
|---|---|---|---|---|---|---|---|---|
| | | | | | Time 0 | Day 11 | Day 20 | Day 32 |
| RR303LN-79-108 | 10% trehalose only | 3.9 | 5 mM gly-HCl | Hazy | NA | NA | NA | NA |
| RR303LN-79-109 | 0.1% taurine/ 0.1% betaine | 5.0 | 5 mM gly-HCl | Hazy | NA | NA | NA | NA |
| RR303LN-79-110 | 0.1% taurine/ 0.1% b-alanine | 5.0 | 5 mM gly-HCl | Hazy | NA | NA | NA | NA |
| RR303LN-79-111 | 0.01% TEA-HCl/ 0.1% b-alanine | 4.9 | 5 mM gly-HCl | Hazy | NA | NA | NA | NA |
| RR303LN-79-112 | 0.01% TEA-HCl/ 0.1% betaine | 3.9 | 5 mM gly-HCl | Hazy | NA | NA | NA | NA |
| RR303LN-79-114 | 10% trehalose only | 4.4 | 5 mM Citrate | Hazy | NA | NA | NA | NA |
| RR303LN-79-115 | 10% trehalose only | 3.5 | 0.25 mM HCl | Hazy | NA | NA | NA | NA |
| RR303LN-79-116 | No trehalose | 3.5 | 0.25 mM HCl | Hazy | NA | NA | NA | NA |
| RR303LN-90-117 | 10% trehalose only | 4.45 | 5 mM tartrate | hazy | NA | NA | NA | NA |
| RR303LN-90-119 | 10% trehalose only | 4.32 | 5 mM lactate | clear | 95.88 | 93.15 | 91.35 | 89.52 |
| RR303LN-90-120 | 10% trehalose only | 3.85 | 5 mM maleate | clear | 95.62 | 72.07 | 66.33 | 66.35 |

EXAMPLE 5

Similar to examples 1 and 2, rhGDF-5 was formulated at 0.1 mg/mL, but using 10 mM acetate buffer at pH 4.5 for example 5. The samples had 10% trehalose added to adjust the tonicity and were tested with various other excipients. These formulations were also stable at 37 degrees Celsius for 32 days as shown in table 5. FIG. 9 shows a graph of the HPLC main peak % and the % recovery of concentration of the sample having 10 mM acetate buffer at pH 4.5 and 10% trehalose, showing approximately 87% retention of the GDF-5 protein after 32 days storage at 37 degrees Celsius. FIG. 10 shows a graph of the HPLC main peak % and the % recovery of concentration of the sample having 10 mM acetate buffer at pH 4.5 with 0.01% TEA-HCl and 0.1% betaine, also showing approximately 87% retention of the GDF-5 protein after 32 days storage at 37 degrees Celsius.

TABLE 5

Stability of 0.1 mg/mL rhGDF-5 in 10 mM Acetate buffer at pH 4.5 with 10% trehalose and other excipients.

| Sample ID | Other Excipients | pH | Clarity | HPLC Analysis, % main peak | | | |
|---|---|---|---|---|---|---|---|
| | | | | Time 0 | Day 11 | Day 20 | Day 32 |
| RR303LN-79-103 | 10% trehalose only | 4.4 | Clear | 95.27 | 93.00 | 91.18 | 87.38 |
| RR303LN-79-104 | 0.1% taurine/0.1% betaine | 4.4 | Clear | 95.34 | 92.92 | 90.96 | 86.27 |
| RR303LN-79-105 | 0.1% taurine/0.1% b-alanine | 4.5 | Clear | 95.30 | 93.12 | 91.42 | 85.97 |
| RR303LN-79-106 | 0.01% TEA-HCl/0.1% b-alanine | 4.5 | Clear | 94.97 | 94.32 | 91.19 | 86.41 |
| RR303LN-79-107 | 0.01% TEA-HCl/0.1% betaine | 4.3 | Clear | 95.34 | 93.00 | 91.74 | 87.27 |

EXAMPLE 6

Similar to example 5, rhGDF-5 was formulated at 0.1 mg/mL in 10 mM acetate buffer, but at pH 5.0 for example 6. The samples had 10% trehalose added to adjust the tonicity and were tested with various other excipients. These formulations were also stable at 37 degrees Celsius for 32 days as shown in table 6.

TABLE 6

Stability of 0.1 mg/mL rhGDF-5 in 10 mM Acetate buffer at pH 5.0, also tested with 10% trehalose and other excipients.

| Sample ID | Other excipients | pH | Clarity | HPLC Analysis, % main peak | | | |
|---|---|---|---|---|---|---|---|
| | | | | Time 0 | Day 10 | Day 20 | Day 32 |
| RR303LN-90-118 | 10% trehalose only | 4.97 | Clear | 96.15 | 93.66 | 91.63 | 89.26 |
| RR303LN-90-122 | 0.1% taurine/0.01% TEA-HCl | 4.97 | Clear | 96.00 | 93.70 | 91.84 | 89.18 |
| RR303LN-90-123 | 0.1% taurine/0.1% b-alanine | 5.04 | Clear | 95.64 | 93.31 | 91.30 | 88.40 |
| RR303LN-90-124 | 0.15 taurine/0.1% betaine | 4.96 | Clear | 96.13 | 93.68 | 91.10 | 88.86 |
| RR303LN-90-125 | 0.1% taurine/0.1% ectoine | 4.95 | Clear | 95.87 | 93.62 | 91.96 | 89.54 |
| RR303LN-90-126 | 0.01% TEA-HCl/0.1% b-alanine | 5.01 | Clear | 96.02 | 93.51 | 91.65 | 88.79 |
| RR303LN-90-127 | 0.01% TEA-HCl/0.1% betaine | 4.91 | Clear | 94.27 | 93.84 | 91.26 | 89.38 |
| RR303LN-90-128 | 0.01% TEA-HCl/0.1% ectoine | 4.91 | Clear | 95.81 | 92.85 | 91.72 | 89.50 |
| RR303LN-90-129 | 0.01% TEA-HCl/0.1% betaine | 4.98 | Clear | 95.64 | 93.54 | 91.50 | 89.14 |
| RR303LN-90-130 | 0.1% b-alanine/0.1% ectoine | 4.98 | Clear | 95.37 | 93.52 | 91.49 | 88.96 |
| RR303LN-90-131 | 0.1% ectoine | 4.89 | Clear | 95.83 | 93.97 | 91.31 | 89.87 |
| RR303LN-90-132 | 0.1% betaine | 4.89 | Clear | 95.88 | 94.09 | 91.68 | 89.44 |
| RR303LN-90-133 | 0.1% b-alanine | 4.99 | Clear | 96.04 | 93.77 | 91.47 | 89.16 |

EXAMPLE 7

Similar to example 6, rhGDF-5 was formulated at 0.1 mg/mL in 10 mM acetate buffer at pH 5.0. The samples in example 7 had 10% sucrose instead of trehalose added to adjust the tonicity. All of the samples yielded clear solutions and approximately 90% retention of the main peak by HPLC (see table 7).

TABLE 7

Stability of 0.1 mg/mL rhGDF-5 in 10 mM acetate buffer at pH 5.0, with 10% sucrose and other excipients.

| Sample ID | Other excipients | pH | Clarity | HPLC Analysis, % main peak | | | |
|---|---|---|---|---|---|---|---|
| | | | | Time 0 | Day 10 | Day 20 | Day 32 |
| RR303LN-90-121 | 10% sucrose only | 4.98 | Clear | 95.87 | 93.47 | 91.83 | 88.74 |
| RR303LN-90-134 | 0.1% taurine | 4.95 | Clear | 95.73 | 94.59 | 91.69 | 89.12 |
| RR303LN-90-135 | 0.1% ectoine | 4.94 | Clear | 95.69 | 94.11 | 92.03 | 89.22 |
| RR303LN-90-136 | 0.01% TEA-HCl/0.1% b-alanine | 5.01 | Clear | 95.92 | 94.40 | 91.46 | 89.00 |

EXAMPLE 8

Similar to Example 2, rhGDF-5 formulations were prepared at a higher concentration of 0.2 mg/mL rhGDF-5 in 5 mM or 10 mM sodium acetate buffer at pH 5 with 10% trehalose. The formulations were tested under different storage temperatures including 37, 40 and 5° C. The stability results are presented in Table 8.

TABLE 8

Stability of 0.2 mg/mL rhGDF-5 in 5 mM or 10 mM acetate buffer with 10% trehalose at various storage temperatures

| Sample ID | Acetate buffer, pH 5 | Storage temp | pH | Clarity | HPLC Analysis % main peak | | | | SEC % aggregates | |
|---|---|---|---|---|---|---|---|---|---|---|
| | | | | | Time 0 | Day 13 | Day 20 | Day 34 | 7 months | Day 34 | 7 months |
| RR303LN-108G | 5 mM sodium acetate | 37° C. | 5.00 | Clear | 95..01 | 93.40 | 92.02 | 89.48 | — | 2.33 | — |
| RR303LN-108J | 10 mM sodium acetate | 37° C. | 4.98 | Clear | 95.46 | 93.01 | 91.56 | 89.09 | — | 2.07 | — |
| RR303LN-108G | 5 mM sodium acetate | 40° C. | 5.03 | Clear | 95.01 | 92.89 | 89.89 | 86.43 | — | 2.79 | — |
| RR303LN-108J | 10 mM sodium acetate | 40° C. | 4.93 | Clear | 95.46 | 92.18 | 89.77 | 85.47 | — | 2.33 | — |
| RR303LN-108G | 5 mM sodium acetate | 5° C. | 4.99 | Clear | 95.01 | — | — | 95.51 | 92.45 | 0.49 | 0.61 |
| RR303LN-108J | 10 mM sodium acetate | 5° C. | 4.96 | Clear | 95.46 | — | — | 95.66 | 92.53 | 0.36 | 0.49 |

All of the samples yielded clear solutions. The samples stored at 37° C. for 34 days still had approximately 90% retention of the rHGDF-5 protein as determined by HPLC. The rHGDF-5 protein recovery from the 40° C. was slightly lower at approximately 85% recovery. No significant changes were observed with the 5° C. samples for at least 7 months.

The results indicate that rhGDF-5 formulated in acetate buffer with or without other excipients could be stored at 5° C. for long term storage. The formulation could be delivered under the body temperature for over a month. The isotonic liquid rhGDF-5 formulation is more stable at high temperatures, 5 and 37° C. than has been shown previously.

We claim:

1. A composition consisting essentially of a 0.1 to 0.2 mg/mL GDF-5 protein solution in a 5 to 10 mM acetate buffer having a pH of from about 4.2 to about 5.3.

2. The composition of claim 1 further comprising one or more excipients selected from the group consisting of trehalose, sucrose, raffinose, glucose, mannitol, and combinations thereof.

3. The composition of claim 2 wherein the solution is isotonic.

4. The composition of claim 2 wherein the excipient is trehalose.

5. The composition of claim 2 wherein the excipient is sucrose.

6. The composition of claim 2 further comprising an excipient selected from the group consisting of TMAO, TEA-HCl, taurine, β-alanine, betaine, ectoine, HO-ectoine, GABA, and combinations thereof.

7. The composition of claim 6 wherein the excipient is present in an amount of from about 0.01 to about 0.5 weight percent.

8. A method of stabilizing a solution of GDF-5 protein comprising the steps of:
 a. providing a sample of a 0.1 to 0.2 mg/mL GDF-5 protein, and
 b. adding a 5 to 10 mM acetate buffer having a pH of from about 4.2 to about 5.3, thereby providing for a stabilized solution of GDF-5.

9. The method of claim 8, further comprising the step of adding one or more excipients selected from the group consisting of trehalose, sucrose, raffinose, glucose, mannitol, and combinations thereof.

10. The method of claim 9, wherein the excipient is added in an amount sufficient to render the protein solution isotonic.

11. The method of claim 9, wherein the excipient is trehalose.

12. The method of claim 9, wherein the excipient is sucrose.

13. The method of claim 9, further comprising the step of adding one or more excipients selected from the group consisting of TMAO, TEA-HCl, taurine, β-alanine, betaine, ectoine, HO-ectoine, GABA, and combinations thereof.

14. The method of claim 13 wherein the excipient is present in an amount of from about 0.01 to about 0.5 weight percent.

* * * * *